United States Patent [19]

Sung et al.

[11] 4,285,823

[45] Aug. 25, 1981

[54] DIESEL LUBRICANT CONTAINING 5-AMINO TETRAZOLES

[75] Inventors: Rodney L. Sung, Fishkill; Benjamin H. Zoleski, Beacon, both of N.Y.

[73] Assignee: Texaco Inc., White Plains, N.Y.

[21] Appl. No.: 109,701

[22] Filed: Jan. 4, 1980

[51] Int. Cl.³ .............................................. C10M 1/32
[52] U.S. Cl. ................................ 252/50; 252/51.5 R; 252/390
[58] Field of Search .................... 252/50, 51.5 R, 390

[56] References Cited

U.S. PATENT DOCUMENTS

| | | | |
|---|---|---|---|
| 3,382,087 | 5/1968 | Ostrowski | 252/390 X |
| 3,909,428 | 9/1975 | De Vries et al. | 252/50 X |
| 4,169,799 | 10/1979 | Sung et al. | 252/42.7 |
| 4,171,269 | 10/1979 | Sung et al. | 252/42.7 X |

*Primary Examiner*—Andrew Metz
*Attorney, Agent, or Firm*—Carl G. Ries; Robert A. Kulason; Henry W. Archer

[57] ABSTRACT

A diesel lubricant composition comprising a lubricating oil base and a corrosion-inhibiting amount of an N-substituted 5-amino-1H-tetrazole.

3 Claims, No Drawings

DIESEL LUBRICANT CONTAINING 5-AMINO TETRAZOLES

BACKGROUND OF THE INVENTION

1. Field of the Invention

This invention relates to a diesel lubricant composition. More especially, the invention relates to silver corrosion inhibitors for diesel lubricant compositions. More particularly, the invention relates to a diesel lubricant composition with improved ability to protect the silver plated areas of a railway diesel engine such as the piston pin insert bearing-carrier combination.

2. Discussion of Prior Disclosures

Lubricant compositions of the type considered here are described in coassigned U.S. Pat. Nos. 4,169,799 and 4,172,269, the disclosures of which are incorporated herein by reference for their showing of railway diesel engine lubricant constitutents.

To elaborate on the background of the present invention, it has been found that railway diesel engine oils having a high degree of alkalinity, that is a TBN of at least 6, are particularly desirable in that they prevent corrosion by oil-soluble acids formed by oxidative deterioration at the high temperature existing under normal conditions of engine employment in proximity to the combustion chamber. The term "TBN" or nominal "TBN" as employed herein refers to "total base number" defined as the quantity of acid, expressed in terms of the equivalent number of milligrams of potassium hydroxide that is required to neutralize all basic constituents present in one gram of a given sample. The method of evaluation is described in ASTM Method D 664. While the foregoing alkalinity can be attained by introduction into the lube oil of a nominal 300 TBN forty percent to fifty percent overbased calcium sulfonate in a naphthenic oil carrier, the resulting lubricant compositions are unsatisfactory because these overbased materials degrade the silver protection characteristics of the oil, a factor of particular significance with respect to railway diesel engines, the vast majority of which, in the United States, and to a significant extent outside of the United States, as well, utilize silverplated piston pin insert bearings.

As described in the above-mentioned patents, particularly useful lubricant compositions are those containing substantially normal and/or highly overbased sulfurized calcium alklyphenolate and highly overbased alkaline earth metal sulfonate additives having a TBN of at least 10 and thus capable of preventing corrosion by oil-soluble acids formed by oxidative deterioration at the high temperatures existing under normal conditions of engine use in proximity to the combustion chamber. Where a sulfurized naphthenic oil-containing composition (having a sulfur content by weight of at least 1 percent) is incorporated with the foregoing overbased additives, the destruction of the silver protective properties of the lubricant oil by the overbased calcium alkylphenolate is overcome, but not the similarly destructive properties of the alkaline earth metal sulfonate. Nevertheless, the incorporation of an alkaline earth metal sulfonate in these lubricant oils is most desirable because of the improved engine performance it provides over an extended period of time.

Thus, the production of a finished lubricant oil for use in railway diesel engines having the necessary degree of alkalinity and, for this purpose, incorporating a normal or highly overbased sulfurized calcium alkylphenolate and an alkaline earth metal sulfonate, without diminution of the silver protective properties of the finished lubricant oil would provide a significant advance in the state of the art.

In accordance with this invention there is provided a diesel lubricating oil composition comprising a diesel lubricating oil containing a silver corrosion inhibiting amount of at least one N-alkylaminomethyl-5-amino-1H-tetrazole.

The composition of the present invention contains the above additive in an amount from about 0.5 to 2.0 weight percent, preferably between 0.5 and 1 weight percent and especially at least 1 percent by weight.

The preparation of the reaction product used in a diesel lubricating composition according to the invention is relatively uncomplicated and can be economically conducted. An N-alkyl-1,3-propanediamine wherein the alkyl group has from 12 to 18 carbon atoms, formaldehyde and 5-amino tetrazole are reacted in substantially equimolar amounts to form the desired products.

The reaction is facilitated by the use of a solvent for the reactants which is inert to the reactants and to the reaction product. A broad range of inert organic, aromatic and aliphatic solvents are suitable for this purpose including xylene and methanol; preferably a mixture of xylene and methanol is used.

The reaction is broadly conducted at a temperature in the range of room temperature to about 150° C., preferably 50° to 100° C. In practice, it is convenient to conduct the reaction at the reflux temperature of the solvent or solvent mixture employed for the reaction.

Suitable N-alkyl-1,3 propanediamines are those available commercially under the name of Duomeens (a product of Armak Co.) wherein the alkyl group is straight chain with an average of 12 to 18 carbon atoms and is attached to the nitrogen through the second carbon in the chain. Examples of suitable N-alkyl-1,3-propanediamine include N-oleyl-1,3-propane diamine (Duomeen O), N-stearoyl-1,3-propanediamine and N-tallow-1,3-propanediamine (Duomeen T).

The reaction product is believed to have the formula:

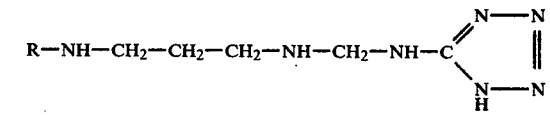

wherein R is a straight chain alkyl having 12 to 18 carbon atoms as above set forth.

In the preparation of the corrosion inhibitor, 5-amino tetrazole, formaldehyde and the diamine are condensed at a temperature ranging from room temperature to about 150° C. until a substantial completion of the reaction. The reaction is conducted in the absence of any catalyst, but generally in the presence of a solvent or diluent or mixture thereof to facilitate the reaction. The solvents or diluents are compatible with the components of the diesel crankcase lubricating oil.

In order to more fully illustrate the nature of the invention and the manner of practicing the same, the following examples are presented.

EXAMPLE I

Preparation of (1-Duomeen T Methyl) 5 Amino-1H-Tetrazole

To a mixture of 0.2 mole of 5 amino-1H-tetrazole, 0.2 mole of Duomeen T, 60 parts methanol and 60 parts of xylene, at reflux temperature, 0.2 mole of formaldehyde was added dropwise. After addition was completed, the mixture was refluxed for 1¾ hr. more, allowed to cool and 100 parts of xylene was added. The mixture was filtered and stripped under vacuum. The reaction product was identified and analyzed by I.R., NMR and elemental analysis.

EXAMPLE II

Preparation of (1-Duomeen O Methyl) 5-amino-1H-tetrazole

Two tenths mole of formaldehyde was added dropwise to a boiling mixture of 0.2 mole Duomeen O, 0.2 mole of 5-amino-1H-tetrazole, 60 parts of methanol and 60 parts of xylene. The mixture was refluxed for 1¾ hr. after addition of formaldehyde was completed. Let cool and 100 parts of xylene was added. The mixture was filtered and stripped under vacuum. The residue was analyzed by elemental analysis, I.R. and NMR.

Samples of a base oil and of the same oil containing different amounts of the additive proposed in Example 1 were tested in what is known to those skilled in the art as the Texaco Modified Silver Disc Friction Test. This procedure is a laboratory test for determining the antiwear properties of a lubricant oil. The test machine comprises a system wherein a one-half inch diameter 52100 steel ball is placed in assembly with three one-half inch silver discs of like size and of a quality identical to that employed in the plating of the silver pin insert bearing of railway diesel engines manufactured by the Electromotive Division (EMD) of General Motors, Inc. These discs are disposed in contact with one another in one plane in a fixed triangular position in a reservoir containing the oil sample to be tested for its silver anti-wear properties. The steel ball is positioned above and in contact with the three silver discs. In carrying out these tests, the ball is rotated while it is pressed against the three discs at the pressure specified and by means of a suitable weight applied to a lever arm. The test results are determined by visual reference, using a low power microscope, to the scars on the discs, the scar texture, whether scored or smooth, for example, and coloration, in a rating system using a standard for comparison and a classification of "poor," "fair," "good" and "excellent."

The rotation of the steel ball on the silver discs proceeds for a period of 30 minutes at 600 revolutions per minute under a 60 kilogram static load. Each oil is tested at 300° F., 400° F., 450° F., and 500° F.

TABLE I

| SILVER DISC FRICTION TEST RESULTS | | | | |
|---|---|---|---|---|
| Blends | A | B | C | D |
| Components wt % | | | | |
| Naphthenic mineral oil of viscosity 300 at 100° F. | 3.00 | | | |
| Paraffin mineral oil | 60.00 | | | |
| Naphthenic mineral oil of 75-80 viscosity at 210° F. | 29.70 | | | |
| Phosphosulfurized polyisobutylene dispersant | 4.10 | | | |
| Calcium sulfurized alkyl phenolate detergent | 3.20 | | | |
| Silicone Foam inhibitor | 150 | | | |
| Oil A | | 99.5 | 99.0 | 98.0 |
| Product of Ex. 1 | | 0.5 | 1.0 | 2.0 |
| Silver Disc Function Test Rating | Poor | Excell. | Excell. | Excell. |

From the data above, it is seen that the present additives are effective corrosion inhibitors for diesel lubricating oil compositions.

More specifically, in Table I, blend "A" is a fully formulated diesel engine oil except that it does not contain a silver corrosion inhibitor. Under the text conditions, additions thereto of 0.5 to 2.0 percent of the additive of the invention to form blends "B", "C", and "D", cause the rating of the oil to pass from "poor" to "excellent".

It will be evident that the terms and expressions employed herein are used as terms of description and not of limitation. There is no intention, in the use of these descriptive terms and expressions, of excluding equivalents of the features shown and described, or portions thereof, and it is recognized that various modifications are possible within the scope of the invention claimed.

What is claimed is:

1. A diesel lubricant composition comprising a diesel lubricating oil and a silver corrosion-inhibiting amount of at least one compound of the formula:

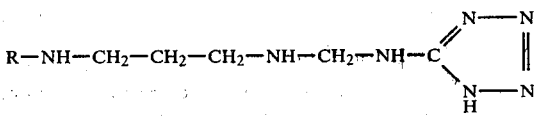

wherein R is a straight chain alkyl having from 12 to 18 carbon atoms in the chain, 2. The composition of claim 1 containing from 0.5 to 2.0 weight percent of said compound.

3. The composition of claim 1 wherein said compound is present in an amount of at least 0.5 percent by weight.

* * * * *